United States Patent [19]
Ryerson

[11] 4,243,631
[45] Jan. 6, 1981

[54] SOLID STATE SENSOR

[75] Inventor: John D. Ryerson, Holland Patent, N.Y.

[73] Assignee: Energy for Independence, Inc., Holland Patent, N.Y.

[21] Appl. No.: 63,207

[22] Filed: Aug. 3, 1979

[51] Int. Cl.³ .................. G01N 27/04; H01C 7/00
[52] U.S. Cl. .................. 422/90; 23/232 E; 73/27 R; 324/71 SN; 338/34; 422/98
[58] Field of Search ............. 422/90, 98, 97; 23/232 E; 338/34; 324/71 SN; 73/27; 427/106, 126

[56] References Cited

U.S. PATENT DOCUMENTS

| | | | |
|---|---|---|---|
| 3,611,243 | 10/1971 | Hardtl | 338/34 |
| 3,625,756 | 12/1971 | Taguchi | 338/34 |
| 3,695,848 | 10/1972 | Taguchi | 324/71 SN |
| 3,699,803 | 10/1972 | Sumi et al. | 324/71 SN |
| 3,778,229 | 12/1973 | Webster et al. | 422/98 |
| 4,001,756 | 1/1977 | Heijne | 338/34 |
| 4,039,941 | 8/1977 | Morrison | 422/98 |
| 4,045,178 | 8/1977 | Okiraka et al. | 422/98 |

Primary Examiner—R. E. Serwin
Attorney, Agent, or Firm—Bruns & Jenney

[57] ABSTRACT

A solid state sensor that is ideally well suited for detecting the presence of ozone in an atmosphere under ambient conditions. A metal oxide semiconductor is placed upon a glass substrate by heating the substrate to about 1200° F. and then depositing molten granules of the metal oxide upon the heated substrate whereby the granules become fused to the substrate and each other to form a rough textured coating. The oxide coating is machined to a desired thickness using any one of many suitable machining operations.

19 Claims, 3 Drawing Figures

SOLID STATE SENSOR

BACKGROUND OF THE INVENTION

This invention relates to a solid state sensor and, in particular, to a solid state sensor wherein a semiconductive coating is fused onto a support material.

More specifically, this invention relates to a solid state sensor for detecting small amounts of ozone in an atmosphere, such as ambient air, without interference from background gases that might be present in the atmosphere, and is an improvement of the sensor disclosed in a pending application, Ser. No. 888,228 filed Mar. 20, 1978.

A gas detector that uses a thin film metal oxide is disclosed in U.S. Pat. No. 3,778,229. However, thin film elements of this nature exhibit an extremely high impedance and are highly susceptible to thermal and random noise. As a consequence, these devices do not lend themselves for use in most practical electronic circuits. The sensitivity of most thin film elements is also relatively low due to the compactness of the semiconductive material and the limited amount of surface area that can be presented to the sampled atmosphere. It is further noted that the equipment required to carry out any type of thin film technology is generally costly and complex which, of course, affects the cost of the products so produced.

Other sensors, particularly those used to detect the presence of reducing gases, have been produced in thick film configurations by means of sintering processes or the like. Although exhibiting a lower impedance than their thin film counterparts, many thin film elements still are slow to respond to oxidizing gases and equally slow to recover once they have been oxidized. As a consequence, these sensors cannot be readily cycled and recycled in a continuous and/or automated sensing system.

Another disadvantage associated with many solid state sensors, both thin film and thick film, is the difficulty encountered in placing the semiconductive coating upon a suitable substrate or support material. Because of the nature of the materials involved, a relatively weak bond is oftentimes formed at the material interface whereupon the semiconductor can flake away from the support or be damaged by ordinary handling.

SUMMARY OF THE INVENTION

It is therefore an object of the present invention to improve solid state sensors for detecting the presence of a gas in an atmosphere.

A further object of the present invention is to improve solid state sensors for detecting the presence of ozone in an atmosphere.

A still further object of the present invention is to improve solid state sensors using a metal oxide semiconductor as a sensing material.

Another object of the present invention is to provide a process for constructing a highly sensitive thick film ozone detector.

Yet another object of the present invention is to provide means for securely bonding a metal oxide semiconductor to a support material to produce a strong and reliable structure.

Still another object of the present invention is to provide a solid state detector containing a semiconductive coating that can be mechanically machined to a desired uniform thickness.

A still further object of the present invention is to provide a solid state ozone detector that is rugged in construction but yet simple and inexpensive to construct.

These and other objects of the present invention are attained by means of a solid state sensor that is constructed of a metal oxide coating that is fused to a glass substrate by first heating the glass to a dull red condition (1200° F.) and then dropping granules of the metal oxide through a flame onto the heated surface of the substrate causing the granules to melt while in transit whereupon striking the substrate, the granules will fuse to the glass and to each other thereby forming a rough textured coating upon the substrate.

In a preferred embodiment of the invention stannous oxide is fused to a quartz envelope to provide a detector element capable of sensing the presence of small amounts of ozone in an atmosphere under ambient temperatures and or pressures.

BRIEF DESCRIPTION OF THE DRAWINGS

For a better understanding of these and other objects of the present invention reference is had to the following detailed description of the invention which is to be read in conjunction with the accompanying drawings, wherein.

DESCRIPTION OF THE INVENTION

A solid state sensor having a relatively thick porous coating of a sensing material fused to a substrate will herein be described with specific reference to using the sensor in detecting the presence of ozone in air. However, it should be noted that the teachings of the present invention have a much broader application and can be utilized in the construction of both oxidizing and reducing sensors utilizing a wide variety of materials.

Preferably, the detecting element 20 utilized in the present invention consists of a hollow quartz rod 21 upon which is fused an outer coating 23 formed of a metal oxide capable of sensing the presence of ozone in an atmosphere under ambient conditions. The coating material is selected from a lower valence form of a multi-valence metal oxide that has the unique ability of reacting with ozone to produce a change in its electrical conductivity that is easily discernible by conventional equipment. When a metalic oxide of this nature comes into reactive contact with ozone, the lower valence oxides are at least partially oxidized to the next higher valence level thereby reducing the number of N-type carriers that are available. This, in turn, results in an increase in the electrical resistance of the sensing material. Stannous oxide has been found to be well suited for use in detecting the presence of ozone in air.

As noted, metal oxides have been used in thin film elements to detect the presence of oxidizing gases. However, these sensors inherently are high impedance devices that must be operated at elevated temperatures in order to produce a reaction. As a result, these devices pick up a good deal of random and thermal noise, respond to background gases at the elevated operating temperatures, particularly to oxygen, and are relatively insensitive to low levels of the gas of interest.

The present sensor avoids many of the physical and electrical problems associated with prior art sensors of this type by providing an extremely rugged solid state device that is capable of operating at ambient temperatures to provide an output signal that is compatible with most standard electronic equipment.

Figure 2:
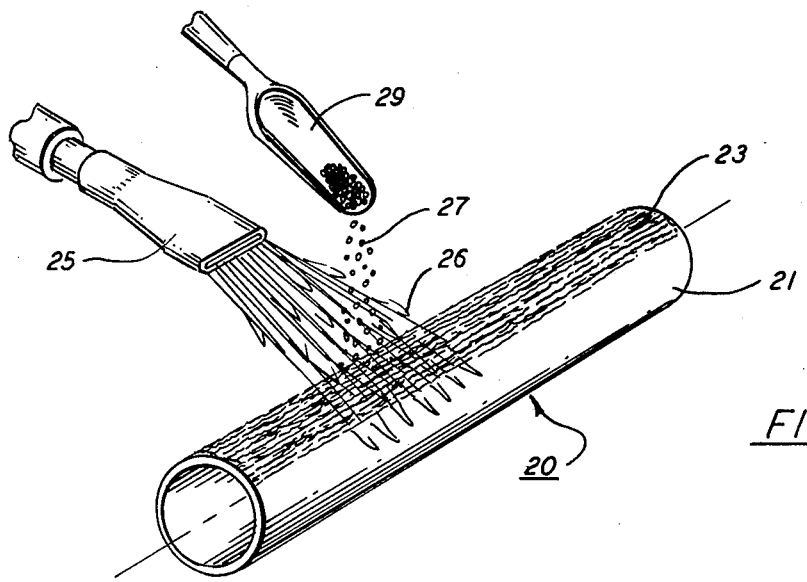
FIG. 2 is a perspective view showing a metal oxide coating being fused to the substrate of the detector illustrated in FIG. 1.

As illustrated in FIG. 2, the quartz rod is heated by means of a torch 25 to bring the color of the rod to a dull red. This occurs when the quartz reaches a temperature of about 1200° F. When the rod is at the desired temperature, the flame front 26 is directed over the top surface of the rod to provide sufficient heat to the rod to hold it at the elevated temperature while at the same time developing a high temperature region directly over the rod. At this time, the amount of oxygen fed to the flame front is cut back to provide a reducing atmosphere within the burning region. Granules 27 of the metal oxide selected for use as a sensing material are gravity fed through the flame front onto the heated rod surface. This can be accomplished by simply sprinkling the granules from a spatula 28 held over the rod or using any other means wherein the particles of material are randomly deposited upon the rod surface.

As the granules pass through the reducing atmosphere of the flame front, the particles in transit are heated to a molten state while they are airborne. Upon striking the quartz rod, the granules fuse to the rod and to each other to create an inextricable bond therebetween. Continued deposition of the material causes a rough textured coating to be established upon the surface of the rod. The exact structure of the coating will vary in response to the random manner by which the molten particles are placed on the rod. However, the coating generally contains a wide variety of hills and valleys having no specific orientation. Each hill is firmly fused at the base to the rod and at the sides to the adjacent hills that surround it. The coating, once cooled, thus provides an extremely strong structure that is tightly bonded to the supporting substrate. Moreover, by use of the present method of fabrication, a rugged solid state device can be easily and inexpensively constructed.

Preferably, the sensing coating of metal oxide should be built up to a thickness of 250,000 angstroms or more using granules that are a little finer than fine table salt. This geometry provides a sufficient number of hills, valleys and even ridges in the coating so that a relatively large surface area is presented to the surrounding atmosphere which enhances the adsorptive properties of the device. It has also been found that a metal oxide sensor of the type herein described attains maximum sensitivity when the coating is held between 200,000 and 250,000 angstroms.

Figure 3:
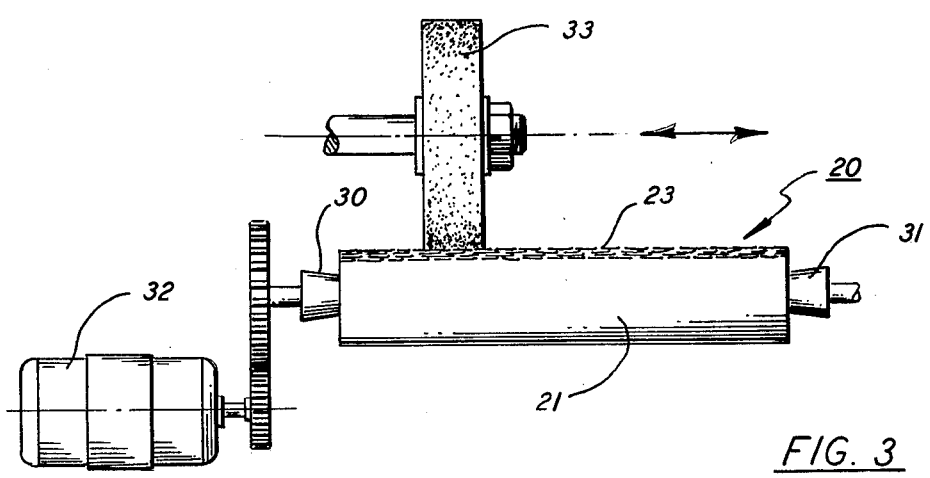
FIG. 3 is a front elevation showing the metal oxide coating being machined to a desired thickness.

Because of the unique way in which the metal oxide is bonded to the quartz substrate, the present oxide coating can be mechanically sized to a desired thickness using many well-known machine shop techniques. As illustrated in FIG. 3 one such technique involves the centerless grinding of the fused detector element. Preferably, the metal oxide coating is placed longitudinally across the rod surface but covers only about 90° of its total circumference to permit the effects of ozone adsorption to be purged photolytically. Coverage of a greater surface area would make it difficult for a radiant source of energy to "see" the entire coated area and the radiation thus could not effectively penetrate or flood the coated area with sufficient light to effectively purge the semiconductor of the ozone effects.

As noted above, the metal oxide coating is built up upon the substrate to a thickness slightly greater than the optimum operating thickness. The coated rod is then positioned between arbors 30,31 of a grinding machine so that it rotates about its axis. The arbors are driven through means of a motor drive 32. A grinding wheel 33, which is properly dressed, is passed axially over the rotating work whereupon one or more precise cuts are taken to bring the coating to the desired thickness range. The thickness of the coating can thus be accurately machined to any desired dimension without difficulty or high cost thus providing the present sensor with a decided advantage over those presently used in the art.

Figure 1:
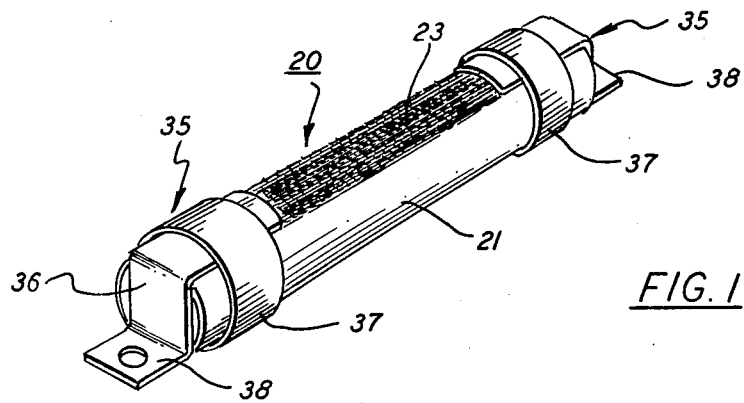
FIG. 1 is a perspective view of one embodiment of a detector encompassing the teachings of the present invention.

Referring once again to FIG. 1, the coated quartz rod is connected at both ends to a combination electrical connector and mounting bracket unit 35. Each bracket unit includes a Z-shaped contact 36 having one horizontal leg thereof held in electrical contact with the coating by means of a clamping band 37. A mounting hole 38 is provided in the opposite leg of contact by which the entire assembly can be secured to a suitable support surface using a threaded terminal.

Although the present invention has been described with particular reference to an ozone detector, it is not necessarily limited to use in this particular application. As should be evident from the present disclosure, many different types of coatings can be applied to a substrate in the manner herein described to create a rugged solid state detector having a rough textured sensing surface capable of ideally adsorbing a gaseous substance. By the same token, the substrate need not be restricted to quartz but can include any number of glass materials that are broadly classified as super cooled liquids and which are able to be fused with the coating material in the manner herein described. It should be further evident that the shape or geometry of the substrate can also vary depending upon the application and the environment in which the sensor is used.

While this invention has been described with reference to the structure disclosed herein, it is not confined to the details set forth and this application is intended to cover any modifications or changes as may come within the scope of the following claims.

I claim:

1. The method of producing a solid state detector including the steps of
    maintaining a glass substrate at an elevated temperature at which the substrate is at least in a semi-molten state,
    heating granules of a semiconductor to a molten state, and
    depositing the molten granules upon the heated substrate whereby the granules fuse to the substrate and to each other in a randomly dispersed manner to provide a rough textured sensing coating thereon.

2. The method of claim 1 wherein said granules are heated by dropping them through a flame onto the heated surface of said substrate whereby the granules melt while they are in transit.

3. The method of claim 2 wherein said flame provides a reducing atmosphere through which the granules fall.

4. The method of claim 1 wherein the substrate is made of quartz that is heated to and maintained at a temperature wherein its surface is a dull red.

5. The method of claim 4 wherein the semiconductor is the lowest valence oxide form of a multi-valent metal oxide.

6. The method of claim 4 wherein the semiconductor is stannous oxide.

7. The method of claim 1 further including the step of connecting a pair of electrical contacts to the coating whereby an electrical current can be passed therethrough.

8. The method of claim 1 further including the step of machining the coating to a desired uniform thickness after it has cooled.

9. The method of claim 8 further including the step of machining the coating to a thickness of between 200,000 and 250,000 angstroms.

10. A detector for sensing the presence of ozone in an atmosphere including
a quartz substrate
granules of a lower valence oxide of a multi-valence metal oxide that is capable of sensing the presence of ozone in an atmosphere randomly fused to the quartz substrate and to each other to provide a rough textured sensing coating on said substrate, and
a pair of electrical connections in contact with the coating to permit a current to be passed therethrough.

11. The detector of claim 10 wherein the substrate is a hollow quartz cylinder and the coating extends longitudinally along the length thereof and covers about 90° of its circumference.

12. The detector of claim 11 wherein the coating is formed of stannous oxide.

13. The detector of claim 12 wherein the stannous oxide coating is between 200,000 and 250,000 angstroms thick.

14. The detector of claim 11 wherein the quartz is transparent to light.

15. A solid state detector for sensing the presence of a gas in an atmosphere that is produced by maintaining a glass substrate at an elevated temperature in a semi-molten state, passing granules of a semiconductor through a flame front to melt the granules while they are in transit, and randomly depositing the molten particles upon the heated surface of the substrate to fuse the granules to the substrate and to each other thereby producing a rough-textured metal oxide coating that is securely bonded to the substrate.

16. The product produced by the process of claim 15 that further includes the step of machining the fused coating to a uniform thickness.

17. The product produced by the process of claim 15 wherein said substrate is formed of quartz and said semiconductor is a metal oxide.

18. The product produced by the process of claim 17 wherein the metal oxide is stannous oxide.

19. The product produced by the process of claim 15 wherein a reducing flame is used to develop the flame front to promote melting of the granules while they are in transit.

* * * * *